United States Patent [19]

Sova

[11] Patent Number: 5,256,269
[45] Date of Patent: Oct. 26, 1993

[54] METHOD AND APPARATUS FOR SEPARATING BIOLOGICAL SUBSTANCES AND ORGANIC COMPOUNDS IN SOLUTION

[75] Inventor: Otto Sova, Kosice, Czechoslovakia

[73] Assignee: 908098 Ontario Inc., Oakville, Canada

[21] Appl. No.: 801,759

[22] Filed: Dec. 3, 1991

[30] Foreign Application Priority Data

Dec. 14, 1990 [CA] Canada ............................... 2032255

[51] Int. Cl.$^5$ .................... G01N 27/26; G01N 27/447
[52] U.S. Cl. ............................. 204/299 R; 204/183.2
[58] Field of Search ........................ 204/183.2, 299 R

[56] References Cited

U.S. PATENT DOCUMENTS

| | | | |
|---|---|---|---|
| 861,226 | 7/1907 | Rambaldini | 204/108 |
| 1,069,993 | 8/1913 | Amos | 204/269 |
| 1,630,074 | 5/1927 | Rogers et al. | 204/136 |
| 1,837,519 | 12/1931 | Bleecker | 204/268 |
| 3,240,692 | 3/1966 | Donnelly | 204/183.2 X |
| 3,355,375 | 11/1967 | Badgley | 204/183.2 X |
| 3,616,456 | 10/1971 | Valmet | 204/299 R |
| 3,679,556 | 7/1972 | Doevenspeck | 204/269 |
| 3,901,780 | 8/1975 | Denckla | 204/183.2 |
| 3,951,777 | 4/1976 | Denckla | 204/299 R |
| 4,200,516 | 4/1980 | Pope | 204/302 |
| 4,619,749 | 10/1986 | Nusbaum | 204/288 |
| 4,657,652 | 4/1987 | Hodges | 204/269 |
| 4,680,100 | 7/1987 | Morin | 204/228 |

*Primary Examiner*—John Niebling
*Assistant Examiner*—John S. Starsiak, Jr.
*Attorney, Agent, or Firm*—Kramer, Brufsky & Cifelli

[57] ABSTRACT

A method and apparatus is described for separating materials on the basis of differences in isoelectric points. In one aspect of the invention an electrochemical cell is provided which has a cell compartment having a plurality of interwaterproof compartments. Provided is a cell lid with a plurality of parallel panels which are narrower than the interwaterproof compartments. A pair of spaced electrodes are attached to the lid and insertable into the end compartments. When the lid is placed on the cell, with an appropriate amount of solution in the cell, a convection free current flow path is formed through the solution above the top edges of the compartments and along the sides of the cell between the gaps formed between the cell side walls and the edges of the narrower lid panels. A natural pH gradient is established when material containing the substance to be separated is dissolved in an appropriate solvent, thereby eliminating the need for expensive carrier ampholytes. A potential is applied between the electrodes which produces an electric field through the horizontal flow path thereby acting as a driving force for moving charged species. When the charged species reaches a point in the pH gradient corresponding to the pI of materials, it is neutralized and remains stationary.

29 Claims, 10 Drawing Sheets

METHOD AND APPARATUS FOR SEPARATING BIOLOGICAL SUBSTANCES AND ORGANIC COMPOUNDS IN SOLUTION

FIELD OF THE INVENTION

The present invention relates generally to the method and technique of electric field separation of materials and more particularly to electric field separation of materials in a pH gradient.

BACKGROUND OF THE INVENTION

The movement of charged molecules in an electric field, known as electrophoresis, is the basis of several separation techniques utilized in the separation of large organic macromolecules, such as for example proteins, RNA, DNA and the like. The basis of all the above mentioned technique consists of applying a potential drop across a medium containing the charged molecules. Depending on the charge carried by the molecule, it will be driven toward the electrode of opposite sign relative to that carried by the molecule. Many macromolecules are zwitterions, having charged side chains on their surface which can be either positively or negatively charged. At some particular value of pH, the sum of the positive charges will balance the negative charges and the molecule will be neutral. This value of pH, which is unique for each molecule, is referred to as the isoelectric point, or pI, of the molecule. At this pH, the molecule, being neutral, is immobile in the electric field. At other pH values the molecule will have a mobility dependent on its charge, which in turn depends on the pH, thus the mobility of the molecule will be a function of solution pH. If a molecule is in a solution having a pH $>$ pI, the charge and mobility of the molecule will be negative while for the case when the molecule is in a solution having a pH $<$ pI, its charge and mobility will be positive.

The existence of a unique pI value for macromolecules provides the basis for isoelectric focusing. In this technique, a pH gradient is established in the medium and the molecule, on being driven through this gradient by the electric field, when it reaches the pH equal to its pI value, becomes electrically neutral and stops moving. The usual procedure is to first form the pH gradient by electrophoresing a mixture of carrier polyampholytes through the medium in which the separation is to be effected. These polyampholytes or carrier ampholytes are typically small, mobile, multi-charged polymers and which preferably exhibit a manifold of different pI values spanning the entire pH range. The pH gradient arises due to a concentration gradient which forms in response to the applied electric field. Thus, for the ionic species to achieve an equilibrium condition in the electric potential gradient, a concentration gradient forms which balances the applied field. The smaller and more mobile the ionic species in the medium of interest, the more rapidly the pH gradient will be established. The substance containing the species to be separated is then introduced into the medium whereupon the component species are separated by the action of the electric field. In light of the discussion above, the mobility of the molecule will be a function of its position in the pH gradient. Therefore, because the mobility and charge of a molecule changes sign on either side of the pI of the molecule, when present in a pH gradient with an applied field, the molecule will be driven towards the position in the cell (and there neutralized) having a pH equal to the pI of the molecule, regardless of its initial position or charge in the cell.

The medium for electrophoresis can be either a free electrolyte, porous paper or a gel. A general problem in scaling up any of the electrophoresis techniques for the separation of macromolecules in a free electrolyte is ohmic heating of the electrolyte. Typically, solutions which stabilize molecules such as proteins are usually highly electrically conducting, being respectable ionic conductors, with the result that high current densities are obtained which cause ohmic heating of the electrolyte. This heating sets up convection currents within the electrolyte which act to disrupt the moving boundaries as well as preventing the accumulation of the neutralized proteins in the cell positions having a pH corresponding to their pI values. One method of dealing with this problem is to add a convection suppression component to the medium, such as a chemically inert and electrically neutral species which, when present in sufficient concentration, acts as a convection suppression medium. A drawback to this approach is that an extra purification step is required to separate the purified material from the convection suppression agent. Accordingly, there is a need to provide an electrochemical cell having a structure and geometry which provide a substantially convection free region thereby permitting the efficient separation and isolation of products purified in this way.

In the gel electrophoresis of proteins and other macromolecules, the gel is employed for two main purposes; the first being to suppress convection currents arising due to temperature variations in the medium arising from ohmic heating as pointed out above, and the second being to provide a molecular sieve for aiding in separating the molecules on the basis of size as well as charge. This is possible since the pore size of the gel can be accurately controlled during polymerization of the latter. As with the scale-up of free electrophoresis, the scale up of gel electrophoresis is not practical. While a very powerful and reliable way of accurately separating macromolecules with very similar pI values, gel electrophoresis is only practically and economically capable of separating and producing very small amounts of a pure material, typically nanogram to microgram quantities. Part of the reason for this is the expense of the carrier polyampholytes required to set up the pH gradient. Another reason for the low yields is that in gel electrophoresis, once the gel medium is set up the material to be separated can be applied only at the boundaries of the gel which severely limits the amount of material which can be purified. Accordingly, there is a need to provide a method and apparatus for the large scale industrial separation of materials on the basis of their isoelectric points.

SUMMARY OF THE INVENTION

The present invention provides a method and device for separating large quantities of biological and organic substances which overcomes the disadvantages of the prior art.

The subject invention provides a static cell apparatus for separating materials in an electrically conductive fluid, which apparatus includes a plurality of separate, adjacent non-conducting fluid containers arranged in a horizontal array. There is included a means for establishing a horizontal, continuous current flow path through the fluid between the containers wherein the cross sectional area of the flow path is small compared to the cross sectional area of the cell perpendicular to the current flow in order to suppress convection currents between adjacent containers when the fluid is contained therein. The apparatus includes a pair of spaced electrodes adapted to be coupled to an external power supply. Each electrode is located in a respective one of two of the containers located at opposite ends of the array.

In another aspect of the invention, a static cell apparatus for separating materials in an electrically conductive fluid is provided which apparatus comprises an outer cell container, a plurality of individual interwaterproof, electrically insulating containers mounted within the outer cell container and which are shorter than the outer cell container. There are a plurality of fluid displacement members which are narrower than the interwaterproof containers and are slidably insertable therein for raising the fluid level from below top edges of the fluid containers to a level above these top edges of the fluid containers thus creating a horizontal current flow path between the individual containers. The cross sectional area of the current flow path is small compared to the cross-sectional area of the cell perpendicular to the current flow in order to suppress convection currents. A pair of spaced electrodes are provided which are adapted to be coupled to an external power supply. Each electrode is located in a respective one of two of the fluid containers located at opposite ends of the outer cell container.

In yet another aspect of the invention, there is provided a static cell apparatus for separating materials in an electrically conductive fluid comprising a generally rectangular cell container having a cell bottom, a pair of side panels and a pair of end panels. The cell includes a plurality of spaced and parallel partitions vertically disposed within the cell container between the side panels which form a plurality of interwaterproof cell compartments along the longitudinal direction of the cell. The two end compartments are formed between the first partitions and the end cell panels. These partitions have a shorter height than the cell end and side panels. A cell lid is provided Which comprises a horizontal panel member and a plurality of spaced, parallel and vertically disposed panel members which are secured to the horizontal panel member and are narrower than the cell compartments and into which they are slidably insertable. A pair of electrodes are each located in a respective one of the two end compartments and are adapted to be coupled to an external power supply. An electrical current flow path between the end compartments is established by placing the cell lid on the container so that the vertical panel members displace the fluid from a level below upper edges of the partitions to a level above these upper edges.

In another aspect of the invention, a method of separating materials in a liquid solution on the basis of differences in isoelectric points comprises making up a liquid solution containing a substance to be separated, wherein the conductivity of the solution can be within the range 20-2000 uS/cm but is preferably in the range 200-700 uS/cm and most preferably in the range 300-500 uS/cm. The solution is placed in an electrochemical cell and a substantially convection free current flow path is established between a pair of spaced electrodes. Power is applied to the cell by impressing a bias voltage between the electrodes until the current drops substantially from of its initial value, whereupon the power is turned off and the isolated product collected.

BRIEF DESCRIPTION OF THE DRAWINGS

The invention will now be described, by way of example only, with reference to the accompanying drawings, in which.

DETAILED DESCRIPTION OF THE PREFERRED EMBODIMENTS

Figure 1:
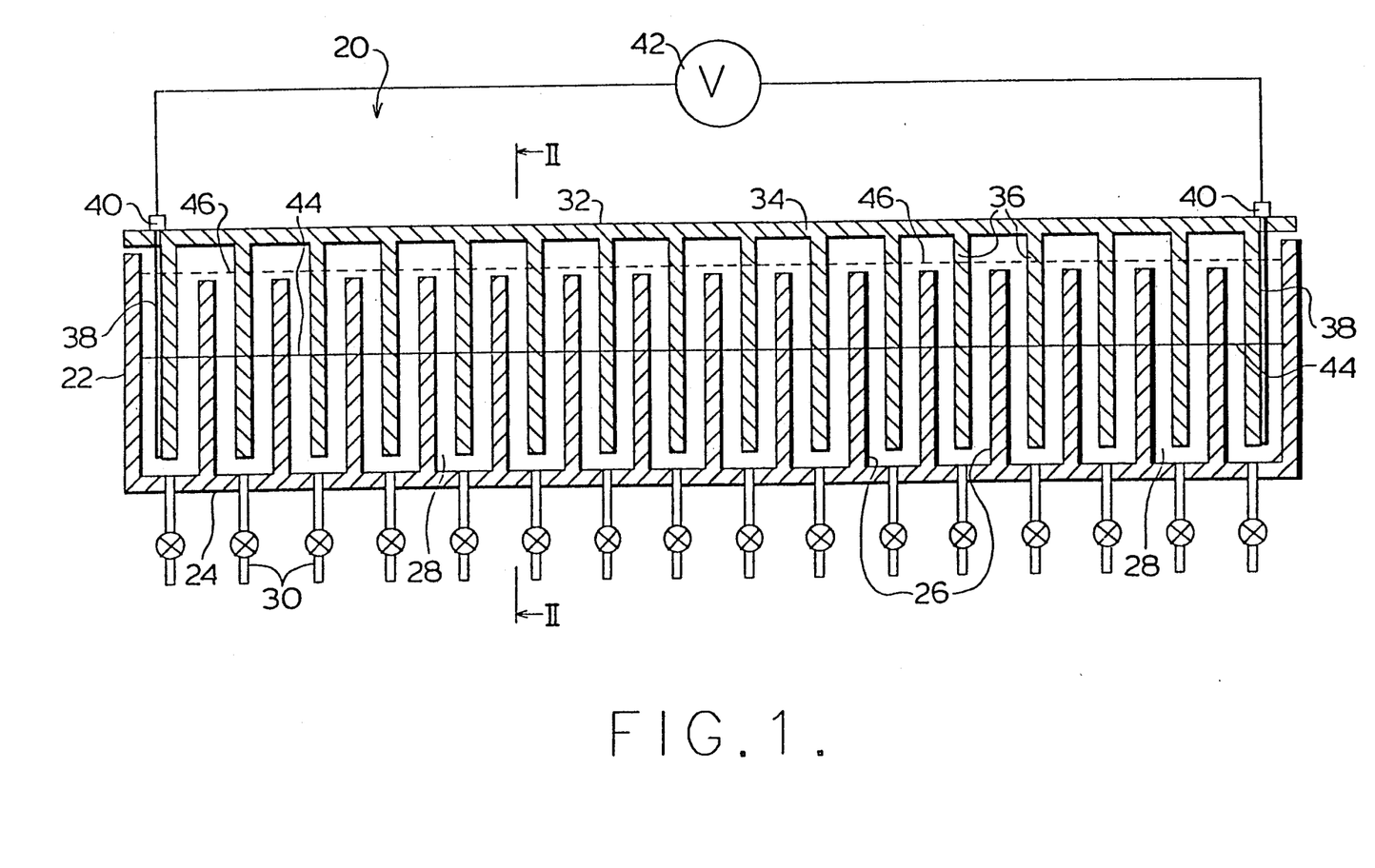
FIG. 1 is a sectional side view of an autofocusing apparatus embodying the subject invention.
Figure 2:
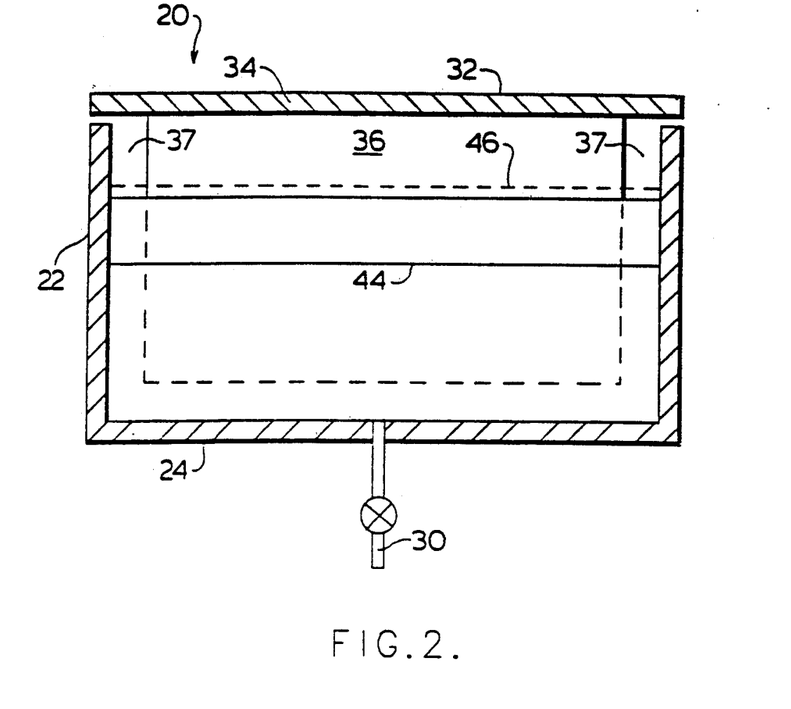
FIG. 2 is an sectional view of the cell taken along the line II—II of FIG. 1.
Figure 3:
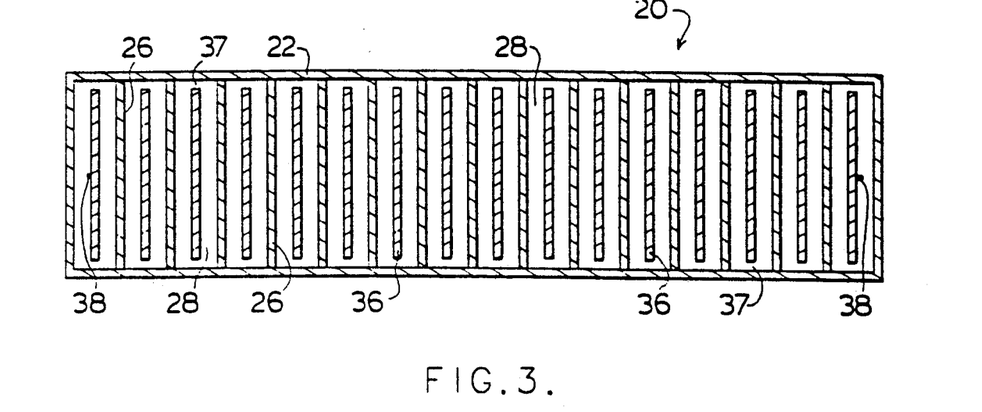
FIG. 3 is a top view of the cell of FIG. 1 with the horizontal portion of the lid cut-away.

Referring first to FIGS. 1, 2 and 3, a preferred embodiment of the autofocusing apparatus of the present invention is illustrated. A static cell 20 comprises a generally rectangular outer container having side and end panels 22 and a bottom panel 24. Cell 20 includes a plurality of parallel, vertical partitions 26 spaced at regular intervals along the length of cell 20. Partitions 26 extend completely across the width of cell 20 thereby dividing the cell into a plurality of individual, adjacent interwaterproof cell compartments 28. Partitions 26 are shorter than the panels 22 which results in compartments 28 being shorter than the cell walls or panels 22. Cell 20 is fabricated from a material which is both electrically insulating or non-conducting and chemically inert. Preferable materials for cell construction include various plastics such as acrylate or Teflon TM to mention a few. In a preferred embodiment, cell 20 is provided with a plurality of drains 30, one associated with each compartment 28. These drains can be omitted entirely in smaller cell units as the fluid in the individual compartments can be removed by devices such as syringes. The number of compartments chosen and the volume of cell 20 itself may be varied depending on the particular application being considered. For some applications the preferred number of compartments is about twenty.

Cell 20 is provided with a lid 32 having a horizontal panel member 34 and a plurality of spaced, parallel, downwardly projecting vertical panel members 36 integrally formed with or rigidly secured to the panel 34 and spaced along the length of lid 32. Panels 36 are aligned so that when lid 32 is placed on cell 20, panels 36 interpenetrate compartments 28 in substantially the central region of each compartment. Panels 36 are narrower in the transverse horizontal direction than compartments 28 and are symmetrically positioned within compartments 28 when lid 32 is placed on cell 20 such that gaps 37 exist between the vertical edges of panels 36 and walls or panels 22 as shown in FIGS. 2 and 3. Cell 20 is provided with a pair of opposed electrodes 38, one located at each end of lid 32 and preferably attached to the outward face of end panels 36. Electrodes 38, which form an anode and a cathode, terminate in electrical connectors 40 located at the ends of lid 32 in order to facilitate coupling the electrodes 38 to an external power supply, shown generally as 42 in FIG. 1. Preferably these electrodes extend vertically in their compartments distance equal to most of the height of their compartments.

Electrodes 38 are preferably chemically inert in the solution of interest as well as being stable against anodic and cathodic dissolution in the same solution under applied bias conditions. Materials such as platinum, various carbons, metals from the class containing nickel and tantalum have been found to perform satisfactorily.

The operation of cell 20 will now be discussed with respect to FIGS. 1, 2 and 3. A mixture containing the material to be separated is dissolved in purified distilled water preferably having a conductivity in the vicinity of 3 uS/cm. The concentration of the starting material initially dissolved in the water is preferably maintained in the range suitable to give a solution with a conductivity in the range of approximately 20 to 2000 uS/cm, but preferably between 200 to 800 uS/cm and most preferably between 300 and 500 uS/cm; the reason the conductivity preferably falls in this range will be discussed below. Cell 20 is then filled with this solution to a level below the tops of partitions 26 indicated by the solid line shown at 44 in FIGS. 1 and 2. Cell lid 32 is lowered into place on cell 20 whereupon panels 36 displace the liquid level to a position above partitions 26 indicated by the broken line shown at 46 in FIGS. 1 and 2. With lid 32 in place and the solution level raised, the two electrodes 38 are immersed in the solution and a horizontal current flow path exists between electrodes 38 along the longitudinal side panels of cell 20 above partitions 26 and through gaps 37. Electrodes 38 are then connected to the external power supply and a direct current (DC) potential drop applied between electrodes 38.

Impurities associated with the material automatically form a pH gradient across the cell when a potential is applied, while the various components making up the material are driven or focused to a position in the cell having a pH corresponding to their pI. Once neutralized at their pI, most components precipitate out of solution dropping to the bottom of the cell compartment. This reduced solubility reflects a reduced electrostatic repulsion at the pI. Depletion of neutralized species in the flow layer will set up a chemical diffusion gradient of unneutralized material which will drive same up to the flow path layer and the process will continue.

Figure 4:
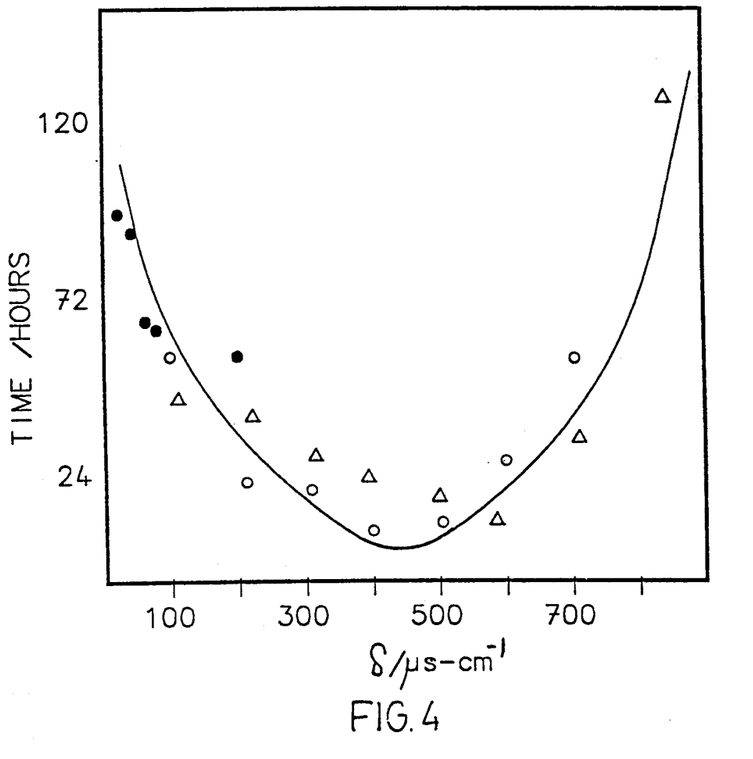
FIG. 4 is a plot of the dependence of separation time on solution conductivity for three different biological materials, (•)-DNA, (/ \)-chloramphenicol, and (o)-bovine serum albumin.

Studies of the operating characteristics of the static cell 20 as a function of volume of the cell and electrolyte conductivity reveal several noteworthy points. First, the time for autofocusing is strongly dependent on the solution conductivity with shortest separation time being achieved for initial solution conductivities of the order of 300–500 uS/cm. FIG. 4 illustrates the dependence of separation time on the initial electrolyte conductivity for three biological materials dissolved in water. Too low of a solution conductivity is representative of too low a concentration which prevents a suitable pH gradient from being produced. This interrelationship between solution conductivity and concentration will be discussed later. On the other hand, too high a conductivity leads to ohmic heating which will result in convection currents being set up in the thin current conduction pathway.

Secondly, the conductivity of the solution changes with time and position within the cell. FIG. 4 also qualitatively illustrates this change in conductivity when the X-axis is relabelled cell compartment number and the Y-axis is relabelled conductivity. This parabolic conductivity curve (which represents the conductivity at the end of a separation experiment wherein initially the conductivity was a uniform horizontal line) shows that the conductivity is a minimum in the middle compartments and is higher in the outer compartments. This decrease in conductivity is due to the concentration of charged species decreasing with time due to neutralization at the pI of the molecule. In addition, charged impurities such as inorganic ions, heavy metals etc. are swept by electromigration to the electrodes of opposite charge in the end compartments thereby increasing the conductivity in the end compartments. The achievement of low conductivity in the middle compartments indicates the separation is complete and this may be monitored directly by in-situ monitoring of solution conductivity or by monitoring the cell current. Accordingly the separation method of this invention should be carried on until the current deceases substantially from its initial value. The inventor has found that as a general rule of thumb, when the cell current drops to less than about 10% of the initial cell current that separation can be considered complete. While the current can in principle decay to zero, the power supply in attempting to maintain a constant power would be required to continue ramping up the voltage. Therefore it will be realized that the value of 10% is somewhat arbitrary. Upon completion of the separation process, the power is switched off and the lid removed from the cell. This acts to drop the solution level below the top edges of the partitions thereby isolating the separated components into the different compartments.

The power which results in optimum operating characteristics, i.e. most rapid separation with minimum ohmic heating is approximately 3 Watts for solution volumes up to 1 liter and for larger volumes a power in Watts which is approximately 50-75% of the volume of the solution in liters. For example, a 10 liter volume would have 5-7.5 Watts applied while a 100 liter volume would have 50-75 Watts applied. It will be understood that these estimates represent upper limits on the cell power on the basis of optimized separation time with respect to heating. However, with certain systems other factors may play a determining role. For example, when applying the method to separation of liquids related to the food industry, undesirable changes in taste and/or chemical composition of various components making up the liquid may result from application of too high a power. In such cases a lower power would be utilized. Because the conductivity decreases overall with time, the cell current also decreases with time. It has been found that maintaining the power level constant gives the best results, therefore it is necessary to ramp the voltage up over time to maintain the applied power constant.

As alluded to above, the static autofocusing apparatus disclosed herein can be readily scaled up from a 0.10 liter cell volume to a 10,000 liter cell volume with little change in cell performance. It is anticipated that the present invention can be used with very large cell volumes, that is volumes substantially exceeding 10,000 liters.

It will be appreciated that the separation process can be carried out at lower temperatures than room temperatures, such as in a cold room. In fact, under certain conditions it may be preferable to carry out the separation at lower temperatures since lowering the electrolyte temperature will also decrease the electrolyte conductivity, thereby allowing higher concentrations to be employed in addition to further reducing ohmic heating. It may also be preferable in certain cases to carry out the separation in the dark, for example with light sensitive materials.

The criteria for selecting a solvent in which to dissolve the material containing the substance to be separated is conductivity and stability. For purification of liquids, stability is not an issue and only the conductivity need be adjusted to fall in the correct range. For purifying solids, the choice of solvent will be made on the basis of stability of the material being purified, in addition to achieving the appropriate solution conductivity. Low conductivity water, (low relative to the solution conductivity) will in general be suitable. Where stability may be a problem, stabilizing additives may be employed. In addition, non-aqueous electrolytes may be employed assuming the species being separated possesses the appropriate solubility therein and the resulting solution has the desired conductivity.

The static autofocusing cell device of the present invention ma be utilized in the separation and purification of many materials. Examples of the application of static autofocusing to the purification of enzymes and food stuffs will now be presented.

EXAMPLE 1

Purification of Peroxidase

The source of peroxidase to be isolated was the horseradish plant. Approximately 500 g of horseradish root was homogenized in 2 liters of water containing 100 mM phosphate buffer at pH 7.0 for 35 minutes and the resulting mixture subjected to centrifugation at 1000 g for 15 min. The resulting supernatant was dialysed against distilled water at 4° C. for 24 h. The conductivity of the solution containing the raw peroxidase was adjusted to 360 uS/cm by addition of low conductivity distilled water. This solution was divided into two parts, one part to be purified using autofocusing followed by gel filtration and the other to be purified using ion-exchange chromatography (IEC). As IEC is a separation technique for separating proteins on the basis of their net charge, this provides a basis for comparison with the autofocusing results.

Figure 5:
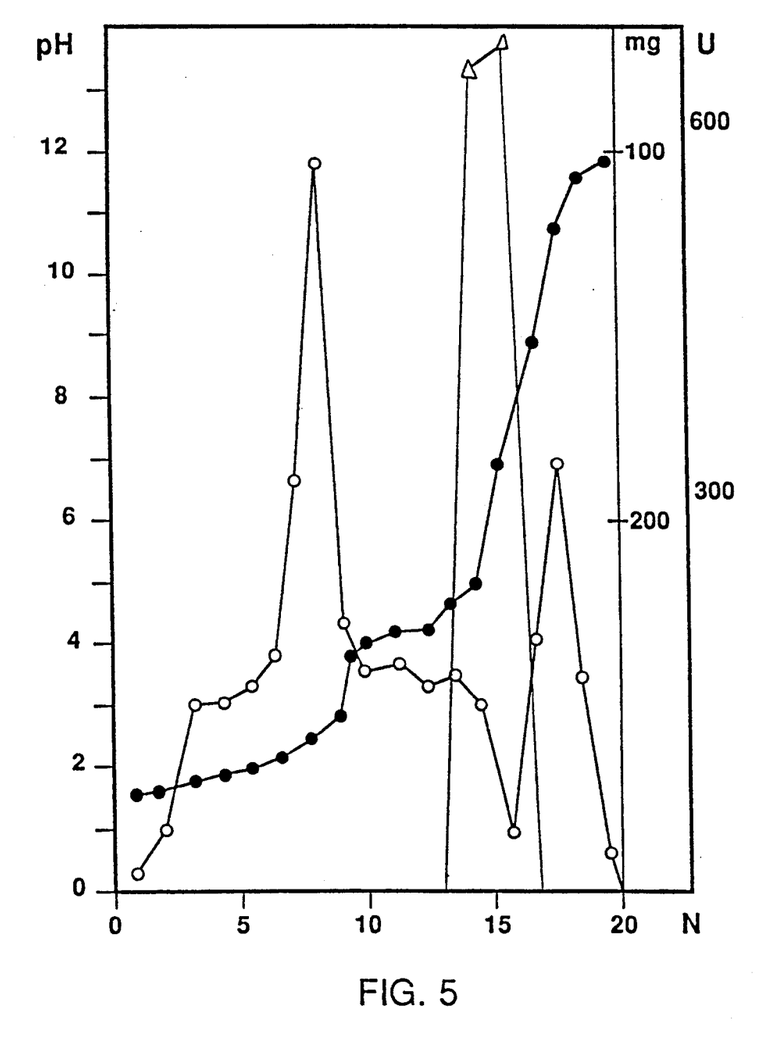
FIG. 5 shows the results of an autofocusing experiment in the purification of peroxidase in a 20 compartment static cell apparatus wherein two plots have been superimposed, (•)-indicates the pH in the compartments, (o)-absorbance of proteins measured at 280 nm, and (/ \)-peroxidase activity measured in international units (U)

For the purification using the method and apparatus of autofocusing disclosed herein, 1 liter of the solution containing the raw peroxidase with a conductivity of 360 uS/cm was poured into a 20 compartment, 1 liter, autofocusing cell and the lid placed thereon. A DC power of 3 Watts was applied for 32 hours at a temperature of 4° C. wherein the voltage was ramped from 250 V to 1000 V DC until the current decreased to its minimum value. FIG. 5 shows the results of the autofocusing experiment. The bulk of the proteins were focused to within the range pH 2.4–3.1 while the fraction containing peroxidase activity focused to within the pH range between 5.00 and 7.12. Those proteins which focused to pH 2.4 to 3.1 are proteins from the plant cell walls and other cellular components contained within the horseradish plant. Those fractions containing the peroxidase are homogenous with respect to isoelectric point of al species contained therein but in general will contain impurity proteins with differing molecular weights. Gel filtration was employed to separate the peroxidase from these other molecular weight components as will now be discussed.

Figure 6:
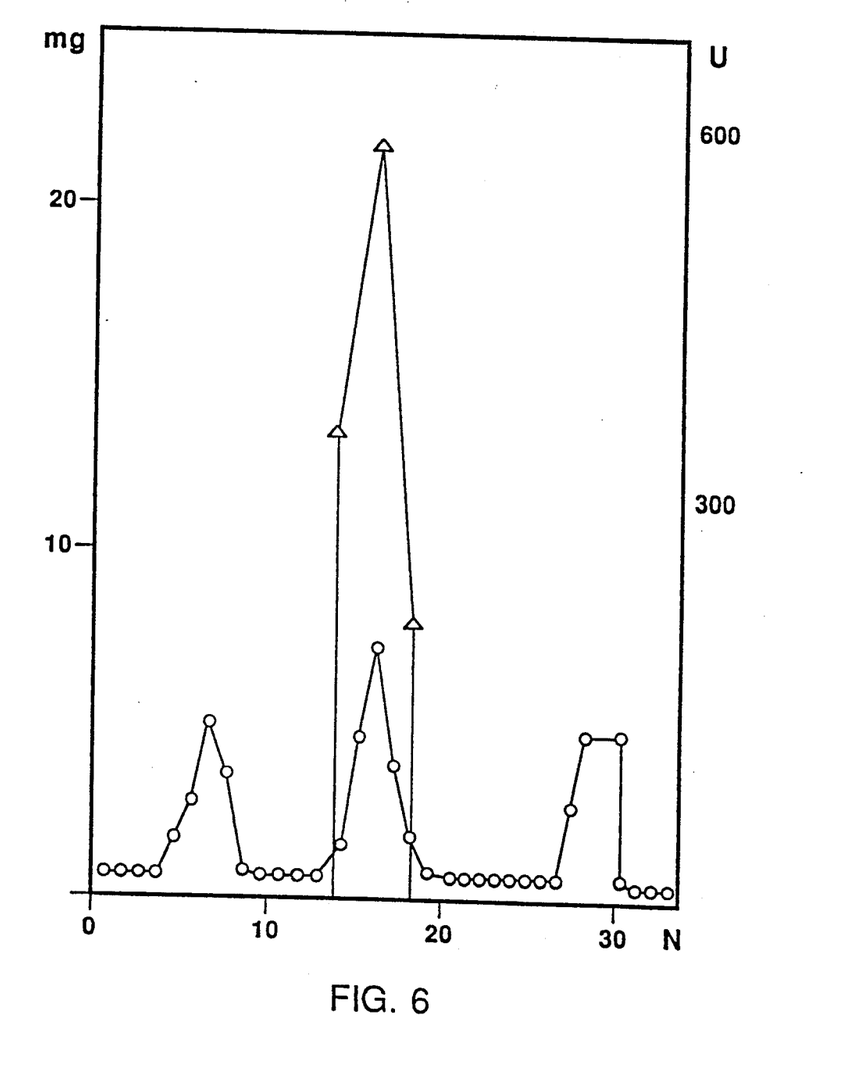
FIG. 6 shows the results of gel filtration of the peroxidase obtained by autofocusing separated by autofocusing in FIG. 5 wherein two plots have been superimposed, (o)-absorbance of proteins at 280 nm and (/ \)-peroxidase activity in international units per mgram (U)

The fractions from the compartments exhibiting peroxidase activity were pooled and loaded onto a Spheron P-40 column (62 cm×3 cm I.D.) and equilibrated with 0.05 M phosphate buffer at pH 7.0. The column was operated at 4° C. at a flow rate of 100 ml/hour and thirty-four 15 ml fractions collected by an automatic fraction collector and tested for peroxidase activity. For peroxidase activity detection, 9 mM pyrogallol and 4 mM hydrogen peroxide solution was freshly prepared in 4 ml of the peroxidase solution and incubated at 30° C. for 5 minutes. The reaction was then stopped by adding 0.2 ml of 100 mM potassium cyanide to the rejection mixture. The absorbance of the resulting yellow brown solution at 380 nm was measured against a blank sample. The protein concentration in individual fractions was determined by the Lowry method. FIG. 6 presents the results of this further separation of the focused peroxidase by gel filtration. The purified enzyme was freeze dried on addition of 25 um glutathione and exhibited activity after 6 months.

For the part which was purified using ion exchange chromatography, a cm-cellulose column (35 cm×2 cm I.D.) was used. The starting eluent solution was a 10 mM sodium acetate buffer made 100 mM with respect to sodium chloride at pH 4.4. The second eluent was 100 mM sodium acetate with 1 M sodium chloride at pH 5.4. A linear gradient was applied at a flow rate of 15 ml/hour and 6 ml fractions were collected in which the peroxidase activity was subsequently determined. The peroxidase active fractions were pooled and subjected to ultrafiltration with disposable Centriflo membrane cones rated at MW 50,000 (for filtrate) and MW 25,000 (for residue).

Figure 7:
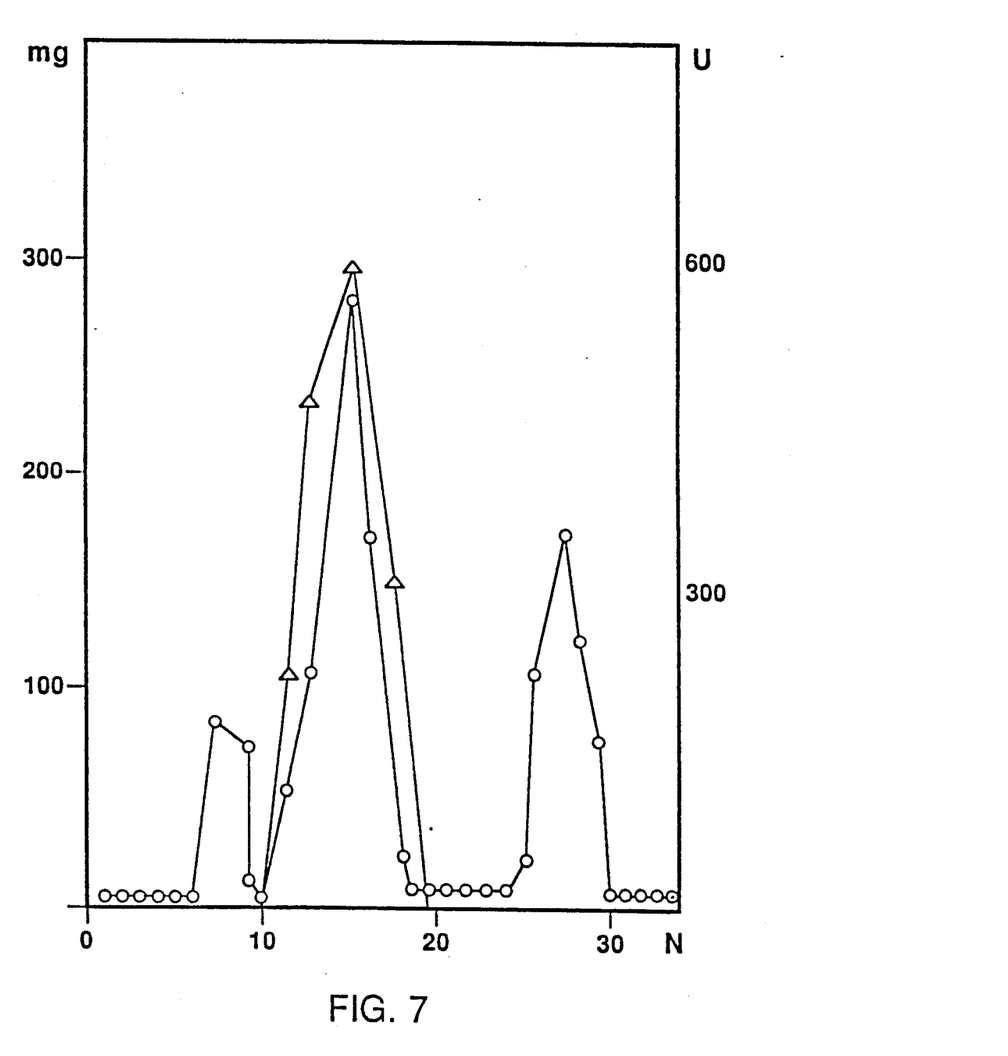
FIG. 7 illustrates the results of purification of peroxidase by ion exchange chromatography (IEC) wherein two plots have been superimposed, (o)-absorbance and (/ \)-peroxidase activity in international units per mgram (U)

FIG. 7 shows the results of purification of peroxidase by ion-exchange chromatography employing a CM-cellulose column.

Comparing autofocusing in conjunction with gel filtration to IEC indicates that with the latter process approximately 71% of the original peroxidase was recovered using autofocusing and after gel filtration the specific activity increased 75 fold and the isolated enzyme was electrophoretically homogeneous. On the other hand, using IEC to separate the peroxidase, only 51% of the peroxidase was recovered while its specific activity increased only 3.24 fold over that of the original solution.

It will be appreciated that the process of separation using autofocusing described herein may be applied several times to the same sample in order to increase the purity of same i.e. to produce a more homogeneous sample with respect to isoelectric point.

The autofocusing apparatus described herein may also be utilized for the purification of neutral, apolar substances from materials containing charged impurities. In this application as applied to solids to be separated, the material containing the apolar substance to be purified is dissolved in suitable water with the concentration in the range suitable to give an initial conductivity in the range of 20-2000 uS/cm while at the same time avoiding precipitation and limitations due to high viscosity. Applying a bias potential between the electrodes results in the charged zwitterionic impurities being autofocused to a position in the cell having a pH corresponding to their respective pI values where they are neutralized while charged inorganic impurities are swept to the end compartments. The apolar component, being electrically neutral, is immobile and hence the purification results by the charged impurities being removed. As applied to liquids, for the method to be successful the liquid should have a conductivity in the range 20-2000 uS/cm. The method will not work very well if the conductivity lies outside this range and therefore this will limit the number of materials which can be separated in this way. However, it may be possible with certain liquids to adjust the conductivity by mixing with a component which will not chemically react with the liquid and which can be readily removed at a later stage following the autofocusing procedure.

Various examples of where this particular application may be utilized is in the separation of alcohols, sugars and the like. Two examples of this will be discussed using examples from the food industry, one a solid and a liquid. The issues of purity and taste quality is of considerable importance both from the perspectives of health and product appeal. For example, to date, undesirable tastes are dealt with in many cases by masking with another harmless substance. Impurities such as heavy metals, pesticide residues and the like pose serious quality control problems in the food industry. Specifically, static autofocusing may be utilized for the preparation of liquids with new tastes, elimination of undesirable tastes in addition to providing a means of standardization of said liquids. Two examples of this application are presented below.

EXAMPLE 2

Purification of Apple Juice

Ten liters of apple juice having a conductivity of 1.2 mS/cm was poured into a suitably sized 20 compartment static autofocuser and a DC power of 5 Watts applied between cathode and anode electrodes 38. The initial voltage was 200 v and the initial current 25 mA. After 48 hours of autofocusing the current dropped down to approximately 10% of its initial value and the power was turned off. Cover 32 was raised from cell 20 which dropped the liquid level below the tops of compartments 28 which divided the solution into 20 separate fractions. These fractions were then drained via drain means 30 and analyzed. The outer compartments were characterized by a higher concentration of heavy metal impurities than the middle compartments.

EXAMPLE 3

Purification of Wine

One hundred liters of wine having a conductivity of approximately 950 uS/cm was poured into a suitably sized 20 compartment static autofocuser and a DC power of 20 Watts applied for 72 hours at 10° C. After this time the current decreased to 10% of its initial value. Lid 32 was then raised thereby isolating the liquid into 20 fractions which were subsequently drained via drain means 30. The lower pH fractions were discarded while re-mixing the higher pH fractions resulted in a better tasting wine.

EXAMPLE 4

Purification of Xylose

Approximately 60 kilograms of crystallized xylose was dissolved in 100 liters of distilled water which gave a solution conductivity of 790 uS/cm. The solution was poured into a 20 compartment, 100 liter volume, static autofocuser and a DC power of 20 Watts applied by impressing a voltage of 1,000 Volts with an initial current of 20 mA. After 72 hours the current decayed to less than 10% of its initial value and the power was turned off. The charge impurities were swept to the compartments containing the anode and cathode electrodes while the purified sugar was removed from the central compartments and subsequently separated from the water by freeze drying or crystallization. The components containing the impurities were then again subjected to autofocusing to increase the yield.

EXAMPLE 5

Purification of Whiskey

A volume of 1.2 liters of commercial whiskey "Five Stars" TM by Seagrams Canada was poured into a suitably sized 20 compartment static cell device constructed in accordance with the invention. The conductivity of the whiskey was 35 uS/cm. The cover was applied and sealed to prevent evaporation of the alcohol. A DC power of 3 Watts was applied to the cell at room temperature. After 24 hours the current decreased to about 10% of its initial value whereupon the power was turned off, the cell lid removed and the 20 different fractions drained off. Due to the apolar nature of the whiskey the alcohol content was the same in all the compartments while the end compartments had a higher concentration of impurities in them. The fractions from the middle compartments were characterized by lower conductivities than the outer compartments. In addition, the fractions in the middle compartments exhibited different colors ranging from light to dark. The contents of the middle compartments were remixed to obtain a lighter tasting and higher quality whiskey than the starting material.

Figure 8:
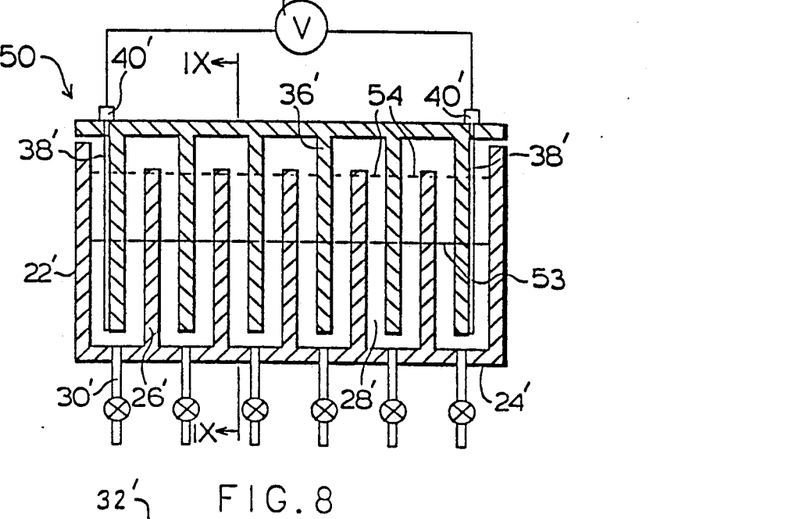
FIG. 8 is a side elevational view of another preferred embodiment of the separating apparatus of the present invention.
Figure 9:
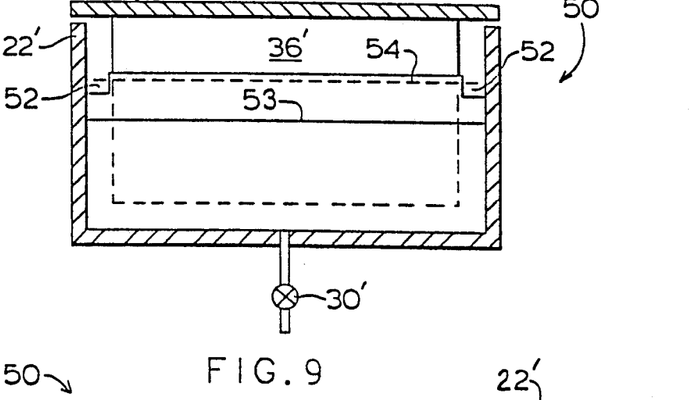
FIG. 9 is an elevational view of the static cell taken along the line IX—IX of FIG. 8.
Figure 10:
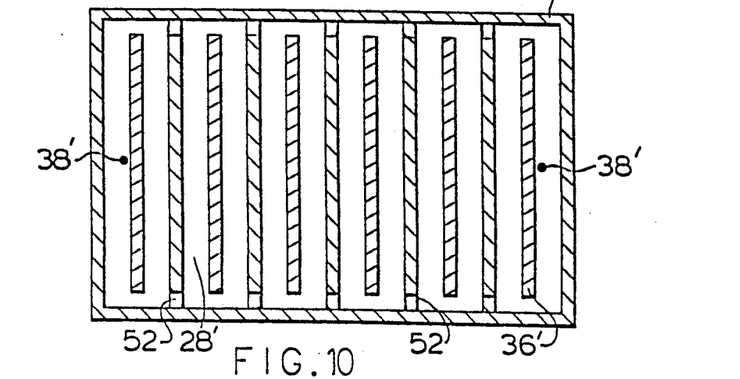
FIG. 10 is a top view of the cell of FIG. 8 with the horizontal portion of the lid cut-away.

Referring now to FIGS. 8, 9 and 10, another embodiment of the static cell apparatus of the subject invention is shown generally at 50 which is similar to cell 20 but with the following differences. Partitions 26' are provided with stepped portions at the top corners where partitions 26' and walls 22' meet, shown generally at 52 in FIGS. 9 and 10. In operation, when lid 32' is placed on cell 50 containing the solution to be purified, the solution level rises from the initial level indicated by the solid line shown at 53 to a level which is just below the top horizontal edge of partition 26' as indicated by the broken line at 54. In other words, the top of the fluid is displaced from the level at 53 below upper edges of the partitions 26' to the level 54 above the upper edges of the stepped portions of the partitions. In this way the current flow path is confined to the longitudinal channel shown in cross section at 52 in FIG. 9.

Figure 11:
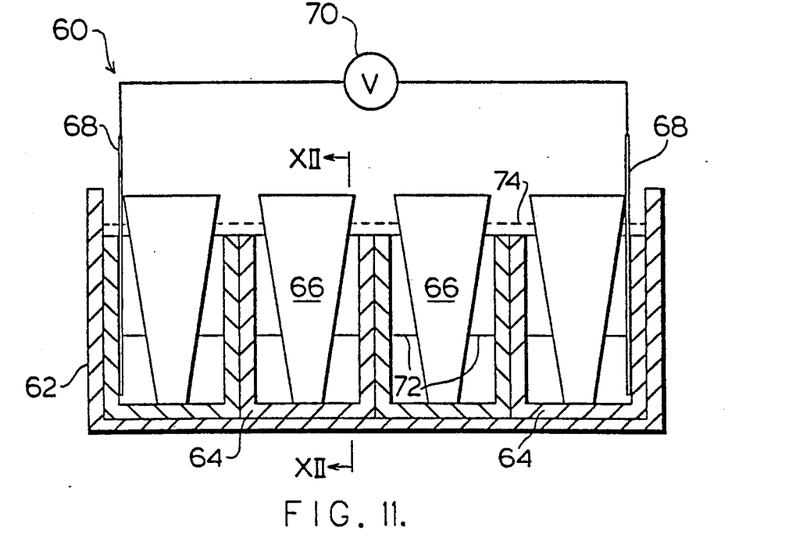
FIG. 11 is a sectional elevation of another embodiment of the autofocusing apparatus of the present invention.
Figure 12:
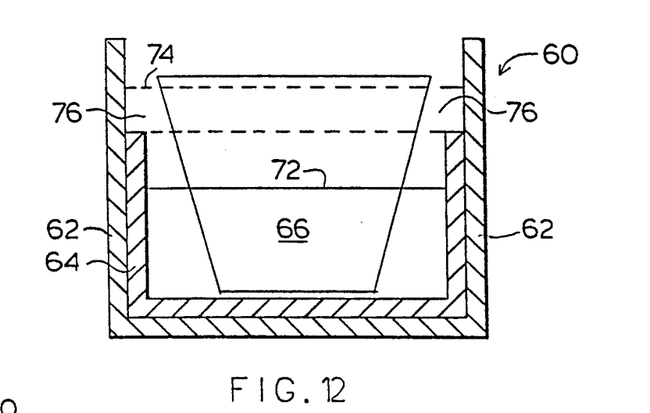
FIG. 12 is a sectional elevation of the autofocusing cell of FIG. 11 taken along the line XII—XII.
Figure 13:
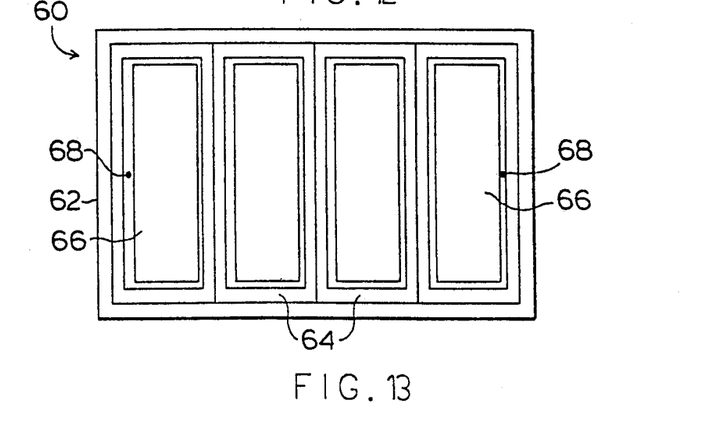
FIG. 13 is a plan view of the cell of FIG. 11.

Referring to FIGS. 11, 12 and 13, yet another embodiment of the static autofocusing cell of the subject invention is shown at 60. Cell 60 includes a main outer cell compartment 62 which is electrically insulating and has a plurality of separate, adjacent, electrically insulating compartments 64 disposed therein. Compartments 64 are shorter than cell compartment 62. Cell 60 is provided with inverted wedge shaped partitions or coulisses 66 which are preferably fabricated of a chemically inert and electrically insulating material such as ceramic. Coulisses 66, when disposed within compartments 64, project above the upper edge of compartments 64, see FIG. 11. Coulisses 66 are narrower than compartments 64 as illustrated in FIGS. 12 and 13. Cell 60 is provided with a pair of electrodes 68, one disposed at each end of the two end compartments. The anode and cathode electrodes 68 are adapted to be coupled to an external power supply 70 as shown in FIG. 11. Coulisses 66 provide convection suppression within cell 60.

In operation, compartments 64 are individually filled with a solution containing the species to be purified to a level below the top edges of compartments 64 as indicated by the solid line shown at 72 in FIGS. 11 and 12. The solution preferably has a conductivity in the range 20-2000 uS/cm and most preferably in the range 300-500 uS/cm. Coulisses 66 are then placed in compartments 64 which results in the solution level rising to a point just above the top edges of compartments 64, as indicated by the broken line shown at 74 in FIG. 11. The current flow paths, shown in cross section at 76 in FIG. 12, are formed between electrodes 68 and extend along the longitudinal sides of cell 60 between coulisses 66 and the inner sides of the static cell 60, see FIG. 11.

Cell 60 may be used instead of cell 20 in applications having stringent material requirements for the cell components. For example, cell 60 may be used for applications in which the cell material cannot be plastic but would preferably be ceramic, such as when the material being purified contains organic species which may be reactive with plastic. In such a case, the design of cell 20 would be clearly inappropriate since construction of such a cell out of plastic would not be practicable. This type of cell has been utilized in the separation of uricase since the latter reacts with many types of plastics.

Figure 14:
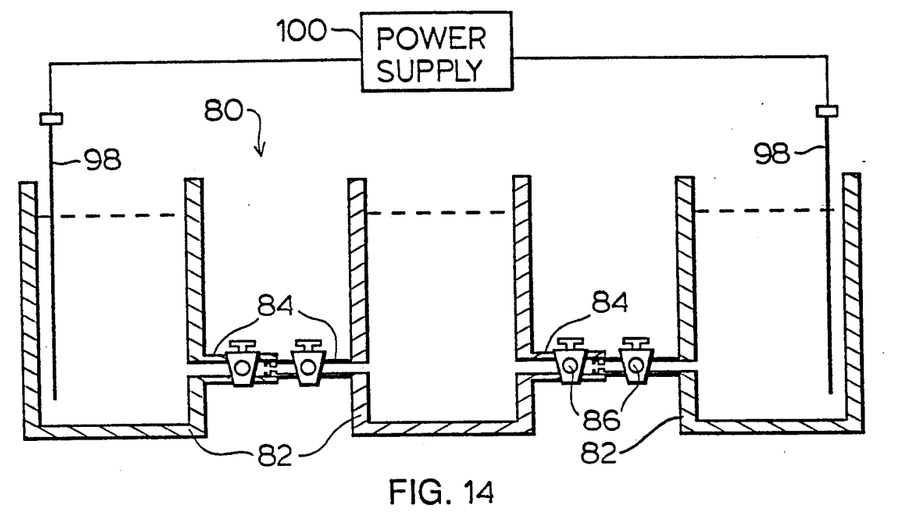
FIG. 14 is a side elevational view of yet another embodiment of the apparatus of the present invention utilizing individual containers.
Figure 15:
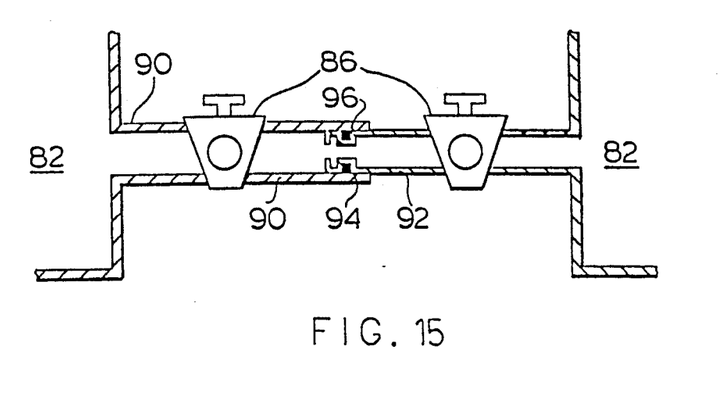
FIG. 15 is a cross sectional view of the inter-compartment coupling of the cell of FIG. 14.

Still another embodiment of the autofocusing apparatus of the present invention is illustrated in FIG. 14 and is shown generally at 80. Cell 80 comprises a plurality of separate, non-conducting fluid containers 82 provided with side wall ports 84 wherein the end containers have one port 84 while the intermediate containers have two diametrically opposed outlet ports 84 each. Outlet ports 84 terminate in on/off valves 86 constructed to also be electrically insulating. Referring to FIGS. 14 and 15, adjacent containers 82 are coupled together by coupling joints 88 comprising tubes 90 and 92 which extend from each valve 86. Tube 92 is provided with an O-ring groove 94 and an O-ring 96 which is adapted to fit tightly into the bore of tube 90, thereby forming a fluid tight seal. Cell 80 is provided with anode and cathode electrodes 98 located and rigidly supported in the end compartments or containers and adapted to be coupled to an external power supply 100. The individual containers 82 provide the convection suppression function performed by partitions 26 and panels 36 in cell 20. This type of static cell is particularly suited to applications wherein large amounts of fluid are being separated into relatively few components. An example of this is the purification and separation of alcoholic beverages such as beer.

In operation, containers 82 are coupled to form fluid tight seals, then filled to the desired level with the solution containing the species being purified. Valves 86 are then opened to form a fluid flow path between the end containers. Electrodes 98 are connected to DC power supply 100 and a bias voltage applied therebetween which results in ionic current flow along the fluid flow path indicated by the broken line shown at 104 in FIG. 14.

Figure 16:
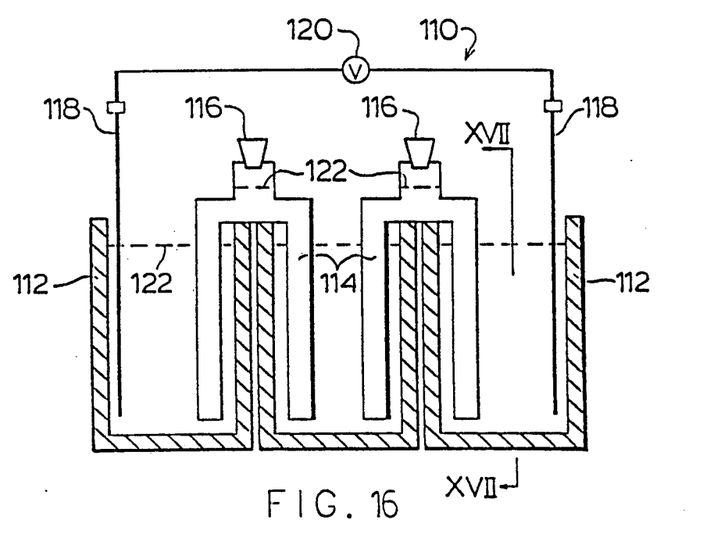
FIG. 16 is a side elevational view of still another embodiment of the apparatus of the present invention.
Figure 17:
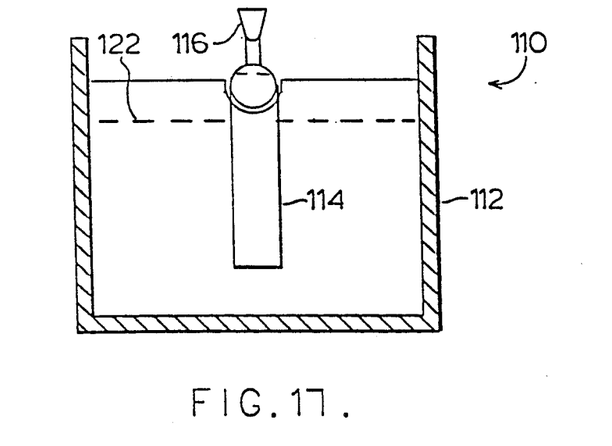
FIG. 17 is a sectional taken along line XVII of FIG. 16.

Referring now to FIGS. 16 and 17, a further embodiment of the static cell autofocusing apparatus of the present invention is shown at 110. Cell 110 includes a plurality of adjacent individual non-conducting containers 112. Containers are adjacently coupled using hollow non-conducting, inverted U-tubes 114. Tubes 114 are provided with air ports 116 to which suction devices may be attached for raising the liquid level in tube 114. It will be understood that ports 116 can be provided with on/off valves to isolate the suction means from the interior of U-tube 114 when the liquid level therein has been raised to the desirable level. Cell 110 is provided with anode and cathode electrodes 118 which are rigidly supported in the end containers and adapted to be coupled to an external power supply 120. In operation, containers 112 and U-tubes are filled to the level indicated by the broken lines at 122 shown in FIG. 16, and a bias voltage is applied between electrodes 118. The DC current flow path is established through fluid filled U-tubes 114. Both the individual containers 112 and U-tubes 114 provide convection suppression within cell 110. After the completion of the separation process as indicated by current drop-off, the power is turned off and the hydraulic couplers or U-tubes 114 are lifted out of the containers in order to isolate the latter. When in use, the preferred U-tubes extend downwardly in their respective containers to a point near the bottom of these containers as shown in FIG. 16.

Figure 18:
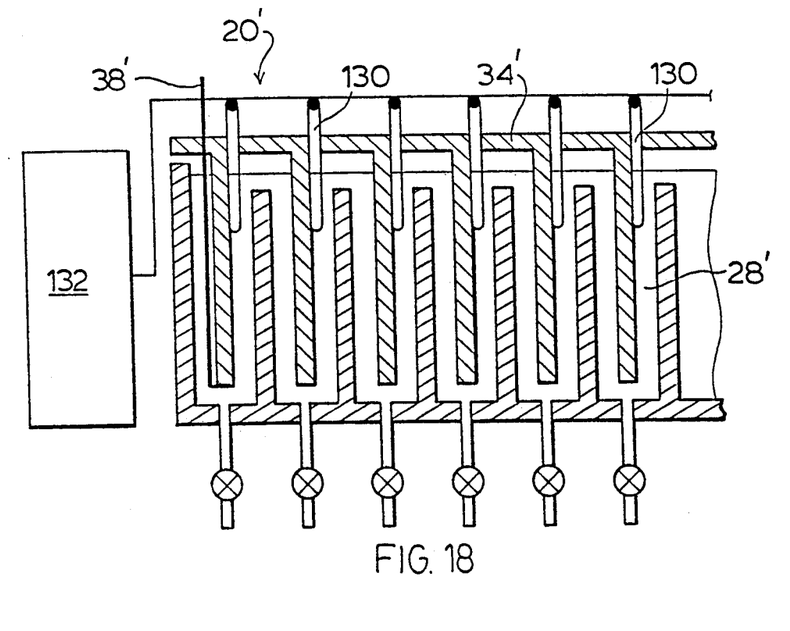
FIG. 18 is a sectional side view of the cell of FIG. 1 broken away showing various sensors attached to the lid for characterizing the solution properties.

It will be understood that various in-situ sensors may be employed for monitoring solution parameters such as temperature, conductivity, pH and UV-visible or infrared absorbance. Considering FIG. 18, a cell 20' which is essentially the same as that of FIG. 1 employs various sensors as mentioned above which may be inserted into individual compartments 28', in much the same way as electrodes 38' are inserted into the end compartments. Specifically, thermocouples 130 for monitoring solution temperature may be inserted through feedthroughs in horizontal member 34' into the individual compartments and monitored via monitor 132. As long as the sensors are displaced away from the current flow path and are chemically inert in the solution, their presence will not perturb the autofocusing process. Conductivity and pH sensors may be similarly coupled to cell 20'. In-situ UV-visible spectra may be obtained by mounting diode array sensors on the alternate sides 22' of cell 20' to monitor the build-up of purified product over time. In this way, the operational parameters of the autofocusing apparatus may be continuously monitored and optimized with respect to one another. For example, for various power levels applied to the cell, the temperature rise can be accurately monitored and the applied power controlled accordingly.

Described now is a possible explanation of why the method and process of autofocusing works in the separation of large quantities of biological materials as shown by the foregoing examples. However such explanation is not deemed to be nor is to be considered limiting with regards to the scope and application of the technique of autofocusing.

There are two factors which each contribute in part to the success of static autofocusing using the method and apparatus disclosed herein. One is related to the autofocusing cell structure while the other relates to the electrochemical nature of the material to be purified.

Referring once again to FIG. 1, the structural factor relates to the presence of a substantially convection free zone created along the top layer of the electrolyte when lid 32 is placed on cell 20. Upwardly projecting partitions 26 and downwardly projecting panels 36 act as baffles thereby preventing convection currents being propagated through cell 20 when power is applied between electrodes 38. It has been determined that the best results are achieved by maintaining the thickness of the current flow path relatively thin with respect to the cross sectional thickness of the cell, optimally between 1-5 mm in thickness.

The chemical factor central to the success of autofocusing as a technique for separating solutions of macromolecules is that the material containing the species to be separated comprises a sufficiently high concentration of macromolecular charged "impurities". The role of these impurities is to provide a natural pH gradient across the cell through which the species of interest are driven and as such they can be viewed as functionally taking the place of the expensive, low molecular weight polyampholytes which are normally pre-dispersed in the transporting medium in classical isoelectric focusing. Thus, when a molecule of the species being isolated reaches a pH corresponding to its pI, it will be neutralized and remain stationary. However, the successful exploitation and utilization of the electrical properties of these impurities for separating and isolating the species of interest is predicated on several conditions being met.

Firstly, there are upper and lower concentration limits on the amount of material which can be separated in this way. The lower concentration limit exists since for the method to work a fairly uniform pH gradient must be set up, thereby requiring a minimum concentration of the "impurity" species. Since the pre-purification process employed to produce the mixtures to be separated will result in a relatively fixed ratio of "impurity" species to species being separated, this implies a minimum concentration of the latter is required. A the other extreme, the upper concentration limit will be determined by one of two factors, one being the necessity to avoid working in saturated solutions which entails working with concentrations sufficiently low such that precipitation does not occur while the second factor is that the solution conductivity must be maintained below a certain value in order to avoid large ohmic heating effects and highly non-uniform pH gradients.

Within this concentration range, the preferable operating concentration will be determined in part by the concentration which gives rise to the optimum electrolyte conductivity. The factors which must be balanced in achieving this optimum conductivity are that the conductivity be low enough to, as mentioned above, minimize ohmic heating losses on the one hand and on the other be high enough to give a stable and as uniform a pH gradient as possible. It will be appreciated that concentration and conductivity are not simply related since the ratio between conductivity and concentration will in general be different for different materials.

Since one aspect of the success of autofocusing is centered around the nature and concentration of the "impurities" associated with the species to be separated, it is clear that to enhance the success of this process special consideration must be given to the process by which the precursor material is pre-purified. As pointed out above, this process is exploiting the electrical properties of the impurity species, and in fact one of the major points of utility of electrophoretic separation techniques in general is that they provide a means of separating species on the basis of charge and mass while isoelectric focusing specifically provides a means for separating species of the same mass but with differing pI values. The salient point is that while special preparation techniques are normally employed to pre-purify a sample to remove impurities on the basis of size and mass prior to isoelectric focusing (which separates species on the basis of pH) such preparation techniques at the very best are unnecessary and at the worst may be detrimental to the success of autofocusing by removing potentially useful impurities.

It will be appreciated that although the electrodes are shown and described as being in the end compartments at opposite ends of the cell, they need not necessarily be in these end compartments. They could be located at intermediate locations if desired but this is normally less desirable since compartments located outside the electrodes would not be used for separation. The pH gradient set up in the solution extends only between the spaced electrodes. Preferably the electrodes should be spaced apart by at least several of the fluid containers.

While the present invention has been described and illustrated with respect to the preferred embodiments, it will be appreciated that numerous variations of these embodiments may be made without departing from the scope of the invention, which is defined in the appended claims.

I claim:

1. A static cell apparatus for separating materials in an electrically conductive fluid on the basis of differences in isoelectric points, comprising:
   a) a plurality of separate, adjacent, non-conducting fluid containers arranged in a horizontal array and adapted to contain said electrically conductive fluid;

b) means for establishing a continuous current flow path through the fluid between the containers, said establishing means comprising fluid flow channels extending between adjacent fluid containers and located below top edges of the containers, the cross sectional area of the flow path being small compared to the cross sectional area of said containers perpendicular to the current flow path in order to suppress convection currents between adjacent containers when said fluid is contained therein;

c) valves provided in said flow channels for stopping flow of said fluid between adjacent fluid containers; and d) two electrodes each located in a respective one of two of said containers wherein the electrodes are adapted to be coupled to an external power supply.

2. A cell apparatus according to claim 1 including an outer cell container, wherein said fluid containers are mounted in the outer cell container and the outer cell container has a greater vertical height than said fluid containers mounted therein.

3. A cell apparatus according to claim 1 further comprising drain means located at the bottom of each fluid container for draining fluid therefrom.

4. A cell apparatus according to any one of claim 1 wherein said electrodes extend vertically in their containers a distance equal to most of the height of their respective end containers.

5. A static cell apparatus for separating materials in an electrically conductive fluid on the basis of differences in isoelectric points, comprising:

a) a plurality of separate, adjacent non-conducting fluid containers arranged in a horizontal array and adapted to contain said electrically conductive fluid;

b) means for establishing a continuous current flow path through the fluid between the containers, said establishing means comprising a plurality of inverted U-tubes each extending from near the bottom of two adjacent fluid containers and over the upper edges of the adjacent containers, the cross sectional area of the flow path being small compared to the cross sectional area of said containers perpendicular to the current flow path in order to suppress convention currents between adjacent containers when said fluid is contained therein; and c) two electrodes each located in a respective one of two of said containers wherein the electrodes are adapted to be coupled to an external power supply.

6. A static cell apparatus for separating materials in an electrically conductive fluid on the basis of differences in isoelectric points, comprising:

a) a plurality of separate, adjacent, non-conducting fluid containers arranged in a horizontal array and adapted to contain said electrically conductive fluid; 'b) means for establishing a continuous current flow path through the fluid between the containers, said establishing means comprising a plurality of fluid displacement members, said displacement members being narrower than the fluid containers and slidably insertable into the fluid containers for raising the fluid level from below top edges of the fluid containers to a level above said top edges or portions of said top edges, the cross sectional area of the flow path being small compared to the cross sectional area of said containers perpendicular to the current flow path in order to suppress convection currents between adjacent containers when said fluid is contained therein; and c) two electrodes each located in a respective one of two of said containers wherein the electrodes are adapted to be coupled to an external power supply.

7. A cell apparatus according to claim 6 including a horizontal panel member, wherein said fluid displacement members comprise a plurality of vertically disposed and spaced panel members secured to said horizontal panel member.

8. A cell apparatus according to claim 7 wherein the electrodes are mounted on the vertical panel members slidably insertable into the two end fluid containers.

9. A cell apparatus according to claim 6 including an outer cell container, wherein said fluid containers are mounted in the outer cell containers and the outer cell container has a greater vertical height than said fluid containers mounted therein.

10. A cell apparatus according to claim 6 wherein the width of said displacement members is less than the internal width of said fluid containers so that gaps are formed between vertical edges of said displacement members and sides of the containers.

11. A cell apparatus for separating materials in an electrically conductive fluid on the basis of differences in isoelectric points, comprising:

a) an outer non-conducting cell container;

b) a plurality of separate, interwaterproof, electrically insulating fluid containers mounted within the outer cell container, said outer cell container having a greater vertical height than the fluid flow containers mounted therein;

c) a plurality of fluid displacement members, said displacement members being narrower than the fluid containers and slidably insertable into the fluid containers for raising the fluid level from below top edges of the fluid containers to a level above said top edges for creating a horizontal current flow path therebetween, wherein the cross sectional area of the flow path is small compared to the cross sectional area of the fluid containers perpendicular to the current flow path in order to suppress convection currents between adjacent fluid containers; and d) two electrodes located in a respective one of two of said fluid containers, which two containers are spaced apart by at least several of said fluid containers, wherein the electrodes are adapted to be coupled to an external power supply.

12. A static cell apparatus according to claim 11 wherein the fluid containers are fabricated from a chemically inert ceramic material and said two electrodes are located at opposite ends of said outer cell container.

13. A static cell apparatus according to claim 11 wherein the fluid displacement members are inverted wedge shaped members.

14. A static cell apparatus according to claim 11 wherein the fluid displacement members are fabricated from ceramic.

15. A static cell apparatus according to claim 11 further comprising a horizontal lid member, wherein the fluid displacement members include a plurality of vertically disposed and spaced parallel panel members secured to the horizontal lid member and said two electrodes are located in the two fluid containers at opposite ends of said outer cell container.

16. A static cell apparatus according to claim 15 wherein said fluid containers are fabricated from a chemically inert plastic material.

17. A static cell apparatus according to claim 11, wherein said fluid containers contain a solution with conductivity in the range of 20-2000 uS/cm.

18. A static cell apparatus for separating materials in an electrically conductive fluid in the basis of differences in isoelectric points, comprising:
   a) a generally rectangular, electrically non-conducting cell container comprising a cell bottom panel, a pair of side panels and a pair of end panels;
   b) a plurality of parallel and spaced, electrically non-conducting partitions vertically disposed within said cell container between the side panels for forming a plurality of individual, adjacent inter-waterproof cell compartments, two end cell compartments being formed between the end panels and the first partitions adjacent thereto, wherein the partitions have a shorter vertical height than the cell end and side panels;
   c) a cell lid comprising a horizontal panel member and a plurality of spaced, parallel vertically disposed panel members secured to the horizontal panel member, wherein the vertical panel members are narrower than the fluid compartments and are insertable into the cell compartments by placing the cell lid on the container;
   d) two electrodes each located in a respective one of said two cell compartments which two compartments are spaced apart by at least several of said cell compartments, the electrodes being adapted to be coupled to an external power supply,
   wherein a substantially horizontal electric current flow path between the two compartments containing the electrodes is established by placing the cell lid on the container so that the vertical panel members displace the fluid from a level below upper edges of said partitions to a level above said upper edges, the current flow path being formed in the fluid displaced above said upper edges of the partitions and between the edges of the vertical panel members and said side panels.

19. A static cell apparatus according to claim 18 wherein the partitions are provided with stepped portions in their top corners forming said upper edges of the partition adjacent said side panels.

20. A static cell apparatus according to claim 18 wherein said cell container contains a solution, made with said fluid, having a conductivity in the range of 20-2000 uS/cm and said electrodes are each located in a respective one of said two end cell compartments.

21. A static cell apparatus according to claim 18 wherein said cell container contains a solution, made with said fluid, having a conductivity in the range of 200-800 uS/cm.

22. A static cell apparatus according to claim 19 wherein said cell container contains a solution, made with said fluid, having a conductivity in the range of 300-500 uS/cm.

23. A static cell apparatus according to claim 18 wherein the electrodes are fabricated from tantalum.

24. A static cell apparatus according to claim 18 wherein the electrodes are fabricated from platinum.

25. A static cell apparatus according to claim 18 wherein each electrode is vertical disposed on an end one of said vertically panel members.

26. A static cell apparatus according to claim 18, wherein said container has at least twenty cell compartments.

27. A static cell apparatus according to claim 18, wherein the cell compartments are provided with drain means located at the bottom of each compartment for draining fluid therefrom.

28. A static cell apparatus according to claim 18, further comprising pH sensors operably coupled to the compartments for sensing the pH of the fluid therein.

29. A static cell apparatus according to claim 18, further comprising conductivity sensors operably coupled to the compartments for sensing the conductivity of the fluid therein.

* * * * *